US010226384B2

(12) United States Patent
Kazala, Jr. et al.

(10) Patent No.: US 10,226,384 B2
(45) Date of Patent: Mar. 12, 2019

(54) ANISOTROPIC DRAPES AND SYSTEMS (71) Applicant: KCI Licensing, Inc., San Antonio, TX (US)

(72) Inventors: Richard Marvin Kazala, Jr., San Antonio, TX (US); Justin Alexander Long, Lago Vista, TX (US); Robert Peyton Wilkes, San Antonio, TX (US); Royce W. Johnson, Green Cove Springs, FL (US)

(73) Assignee: KCI Licensing, Inc., San Antonio, TX (US)

( * ) Notice: Subject to any disclaimer, the term of this patent is extended or adjusted under 35 U.S.C. 154(b) by 618 days.

(21) Appl. No.: 14/867,933

(22) Filed: Sep. 28, 2015

(65) Prior Publication Data
US 2016/0015569 A1 Jan. 21, 2016

Related U.S. Application Data (62) Division of application No. 13/437,898, filed on Apr. 2, 2012, now Pat. No. 9,173,788, which is a division
(Continued)

(51) Int. Cl.
*A61F 13/00* (2006.01)
*A61M 1/00* (2006.01)
(Continued)

(52) U.S. Cl.
CPC .. *A61F 13/00059* (2013.01); *A61F 13/00017* (2013.01); *A61F 13/00029* (2013.01);
(Continued)

(58) Field of Classification Search
CPC .......... A61F 13/00017; A61F 13/00034; A61F 13/00038; A61F 13/00068; A61F 13/0243;
(Continued)

(56) References Cited

U.S. PATENT DOCUMENTS 1,355,846 A 10/1920 Rannells
2,547,758 A 4/1951 Kelling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PHD; Vacuum-Assisted Closure: A new Method for Wound Control and Treatment: Clinical Experience; Annals of Plastic Surgery.
(Continued)

*Primary Examiner* — Adam Marcetich
*Assistant Examiner* — Jessica R Arble (57) ABSTRACT An anisotropic wound drape for treating a wound on a patient includes a flexible sheet for placing over a tissue site. The flexible sheet includes a first isotropic zone, and a second isotropic zone. The first isotropic zone and the second isotropic zone are configured to provide the flexible sheet with anisotropic stretching properties. The anisotropic drape may used as part of a reduced-pressure wound treatment system. Other systems and methods are also presented.

30 Claims, 6 Drawing Sheets

Related U.S. Application Data of application No. 12/475,231, filed on May 29, 2009, now Pat. No. 8,172,816.

(60) Provisional application No. 61/144,067, filed on Jan. 12, 2009, provisional application No. 61/121,362, filed on Dec. 10, 2008, provisional application No. 61/057,797, filed on May 30, 2008, provisional application No. 61/057,798, filed on May 30, 2008, provisional application No. 61/057,800, filed on May 30, 2008, provisional application No. 61/057,802, filed on May 30, 2008, provisional application No. 61/057,803, filed on May 30, 2008, provisional application No. 61/057,805, filed on May 30, 2008, provisional application No. 61/057,807, filed on May 30, 2008, provisional application No. 61/057,808, filed on May 30, 2008, provisional application No. 61/057,810, filed on May 30, 2008.

(51) Int. Cl.
*A61F 13/02* (2006.01)
*A61L 15/60* (2006.01)
*A61H 1/00* (2006.01)
*A61F 15/00* (2006.01)

(52) U.S. Cl.
CPC .. *A61F 13/00034* (2013.01); *A61F 13/00038* (2013.01); *A61F 13/00068* (2013.01); *A61F 13/022* (2013.01); *A61F 13/0209* (2013.01); *A61F 13/0216* (2013.01); *A61F 13/0223* (2013.01); *A61F 13/0243* (2013.01); *A61F 13/0289* (2013.01); *A61F 15/008* (2013.01); *A61H 1/008* (2013.01); *A61L 15/60* (2013.01); *A61M 1/0023* (2013.01); *A61M 1/0088* (2013.01); *A61F 13/00* (2013.01); *A61F 2013/0028* (2013.01); *A61F 2013/0054* (2013.01); *A61F 2013/00131* (2013.01); *A61F 2013/00136* (2013.01); *A61F 2013/00174* (2013.01); *A61F 2013/00182* (2013.01); *A61F 2013/00246* (2013.01); *A61F 2013/00536* (2013.01); *A61F 2013/00748* (2013.01); *A61M 2205/70* (2013.01); *A61M 2207/00* (2013.01); *A61M 2210/1007* (2013.01); *A61M 2210/1021* (2013.01); *Y10T 29/49* (2015.01); *Y10T 29/49826* (2015.01)

(58) Field of Classification Search
CPC ............ A61F 13/00; A61F 2013/00131; A61F 2013/00136; A61M 1/0088
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,121,582 A * | 10/1978 | Masso Remiro ............... A61F 13/00021 602/76 |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | Debusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |

(56) References Cited

U.S. PATENT DOCUMENTS

| | | | |
|---|---|---|---|
| 6,320,093 B1 * | 11/2001 | Augustine | A61F 13/0206 128/888 |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2005/0101940 A1 * | 5/2005 | Radl | A61M 1/0011 604/543 |
| 2007/0032755 A1 * | 2/2007 | Walsh | A61M 1/0088 602/2 |
| 2007/0066946 A1 | 3/2007 | Haggstrom et al. | |
| 2009/0047855 A1 * | 2/2009 | Seth | A61F 13/4902 442/329 |

FOREIGN PATENT DOCUMENTS

| | | | |
|---|---|---|---|
| AU | 755496 B2 | 12/2002 | |
| CA | 2005436 A1 | 6/1990 | |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| GB | 692578 A | 6/1953 | |
| GB | 1574066 A * | 9/1980 | A61B 5/201 |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 2006219776 A | 8/2006 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | WO 9205755 A1 * | 4/1992 | A61F 13/023 |
| WO | 93/009727 A1 | 5/1993 | |
| WO | 94/020041 A1 | 9/1994 | |
| WO | WO 9420152 A1 * | 9/1994 | A61M 1/0084 |
| WO | 96/05873 A1 | 2/1996 | |
| WO | 97/18007 A1 | 5/1997 | |
| WO | 99/13793 A1 | 3/1999 | |
| WO | 03017898 A1 | 3/2003 | |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinoví?, V. ?uki?, Ž. Maksimoví?, ?. Radak, and P. Peška, "Vacuum Therapy in the Treatment of Peripheral Blood Vessels," Timok Medical Journal 11 (1986), pp. 161-164.

F.E. Johnson, "An Improved Technique for Skin Graft Placement Using a Suction Drain," Surgery, Gynecology, and Obstetrics 159 (1984), pp. 584-585.

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

(56) References Cited

OTHER PUBLICATIONS

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

\* cited by examiner

FIG. 7B

ANISOTROPIC DRAPES AND SYSTEMS

RELATED APPLICATIONS

This application is a divisional of U.S. patent application Ser. No. 13/437,898, entitled "Anisotropic Drapes and Systems," which is a divisional of U.S. patent application Ser. No. 12/475,231, entitled "Anisotropic Drapes and Systems," which claims the benefit, under 35 USC §119(e), of the filing of U.S. Provisional Patent Application Ser. No. 61/057,807, entitled "Reduced-pressure Surgical Wound Treatment System," filed May 30, 2008; U.S. Provisional Patent Application Ser. No. 61/057,798, entitled "Dressing Assembly For Subcutaneous Wound treatment Using Reduce Pressure," filed May 30, 2008; U.S. Provisional Patent Application Ser. No. 61/057,808, entitled "See-Through, Reduced-Pressure Dressing," filed May 30, 2008; U.S. Provisional Patent Application Ser. No. 61/057,802, entitled "Reduced-Pressure Dressing Assembly For Use in Applying a Closing Force," filed May 30, 2008; U.S. Provisional Patent Application Ser. No. 61/057, 803, entitled "Reduced-Pressure, Linear-Wound Treatment System," filed May 30, 2008; U.S. Provisional Patent Application Ser. No. 61/057,800, entitled "Reduced-Pressure, Compression System and Apparatus for use on a Curved Body Part," filed, May 30, 2008; U.S. Provisional Patent Application Ser. No. 61/057,797, entitled "Reduced-Pressure, Compression System and Apparatus for use on Breast Tissue," filed May 30, 2008; U.S. Provisional Patent Application Ser. No. 61/057,805, entitled "Super-Absorbent, Reduced-Pressure Wound Dressing and System," filed May 30, 2008; U.S. Provisional Patent Application Ser. No. 61/057,810, entitled "Reduced-Pressure, Compression System and Apparatus for use on a Joint," filed May 30, 2008; U.S. Provisional Patent Application Ser. No. 61/121,362, entitled "Reduced-Pressure Wound treatment System Employing an Anisotropic Drape," filed Dec. 10, 2008; and U.S. Provisional Patent Application Ser. No. 61/144, 067, entitled "Reduced-Pressure, Compression System and Apparatus for use on a Joint," filed Jan. 12, 2009. Each of the applications set forth above are incorporated herein by reference for all purposes.

BACKGROUND

The present invention relates generally to medical treatment systems, and more particularly, to anisotropic drapes and reduced-pressure wound treatment systems and methods employing anisotropic drapes.

Vapor and oxygen permeable isotropic film dressings, frequently called drapes, may be used to cover wounds, or damaged areas of tissue, to facilitate healing and prevent infection. The elasticity of these isotropic drapes is substantially uniform. This can be a problem, however, if one would like to regulate translation or approximation of tissue, such as dermal tissue or subdermal tissue, at a specific rate in one direction and at another rate in another direction. Improper regulation of tissue translation may involve negative side-effects, including, but not limited to, blisters, hyper-pigmentation, as well as many other skin complications and irritations. Other shortcomings may exist as well.

BRIEF SUMMARY

Shortcomings with wound care systems and methods are addressed by the illustrative embodiments as shown and described. According to one illustrative embodiment, a reduced-pressure wound treatment system for treating a tissue site on a patient includes a wound drape that has a flexible sheet with a first isotropic zone and a second isotropic zone. The first isotropic zone and the second isotropic zone are configured to provide the flexible sheet with anisotropic stretching properties. The system also includes a manifold for disposing between the wound drape and the tissue site and a reduced-pressure subsystem for delivering a reduced pressure to the manifold.

According to another illustrative embodiment, a wound drape includes a flexible sheet for placing over a tissue site. The flexible sheet has a first isotropic zone and a second isotropic zone. The first isotropic zone and the second isotropic zone are configured to provide the flexible sheet with anisotropic stretching properties.

According to another illustrative embodiment, a wound drape includes a flexible sheet and an anisotropic member coupled to the flexible sheet. The flexible sheet and anisotropic member are configured to provide the flexible sheet with anisotropic stretching properties such that the flexible sheet stretches more in a first direction than in a second direction.

According to another illustrative embodiment, a wound drape includes a flexible sheet and a fluidly inflatable bladder coupled to the flexible sheet. The flexible sheet and fluidly inflatable bladder are configured to provide the flexible sheet with anisotropic stretching properties such that the flexible sheet stretches more in a first direction than in a second direction. The inflatable bladder may take numerous forms. The wound drape may provide a closing force.

According to another illustrative embodiment, a method for treating a tissue site on a patient with reduced pressure includes disposing a manifold proximate the tissue site, disposing an anisotropic wound drape over the manifold, sealing the anisotropic drape to the patient's epidermis, and fluidly coupling a reduced-pressure source to the manifold. The anisotropic drape includes at least a first isotropic zone and a second isotropic zone such that the anisotropic drape stretches more in a first direction than a second direction.

According to another illustrative embodiment, a method of manufacturing a wound drape includes the step of forming a flexible sheet for placing over a tissue site with a first isotropic zone and a second isotropic zone. The first isotropic zone and the second isotropic zone are configured to provide the flexible sheet with anisotropic stretching properties.

Other features and advantages of the illustrative embodiments will become apparent with reference to the drawings and detailed description that follow.

BRIEF DESCRIPTION OF THE DRAWINGS

A more complete understanding of the present invention may be obtained by reference to the following Detailed Description when taken in conjunction with the accompanying Drawings wherein.

DETAILED DESCRIPTION

In the following detailed description of the illustrative embodiments, reference is made to the accompanying drawings that form a part hereof, and in which is shown, by way of illustration, specific embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the invention, the description may omit certain information known to those skilled in the art. The following detailed description is not to be taken in a limiting sense, and the scope of the present invention is defined only by the appended claims.

Referring now to FIGS. 1-3B, a reduced-pressure treatment system 100 for treating a tissue site, e.g. incision 102, is presented. The reduced-pressure treatment system 100 is presented in the context of a general tissue site that includes an incision 102 and an undermined subcutaneous tissue site 110, but it will be appreciated that the reduced-pressure treatment system 100 may be used to treat many different types of wounds including open wounds or other tissue sites. The tissue site may be the bodily tissue of any human, animal, or other organism, including bone tissue, adipose tissue, muscle tissue, dermal tissue, vascular tissue, connective tissue, cartilage, tendons, ligaments, or any other tissue.

Figure 1:
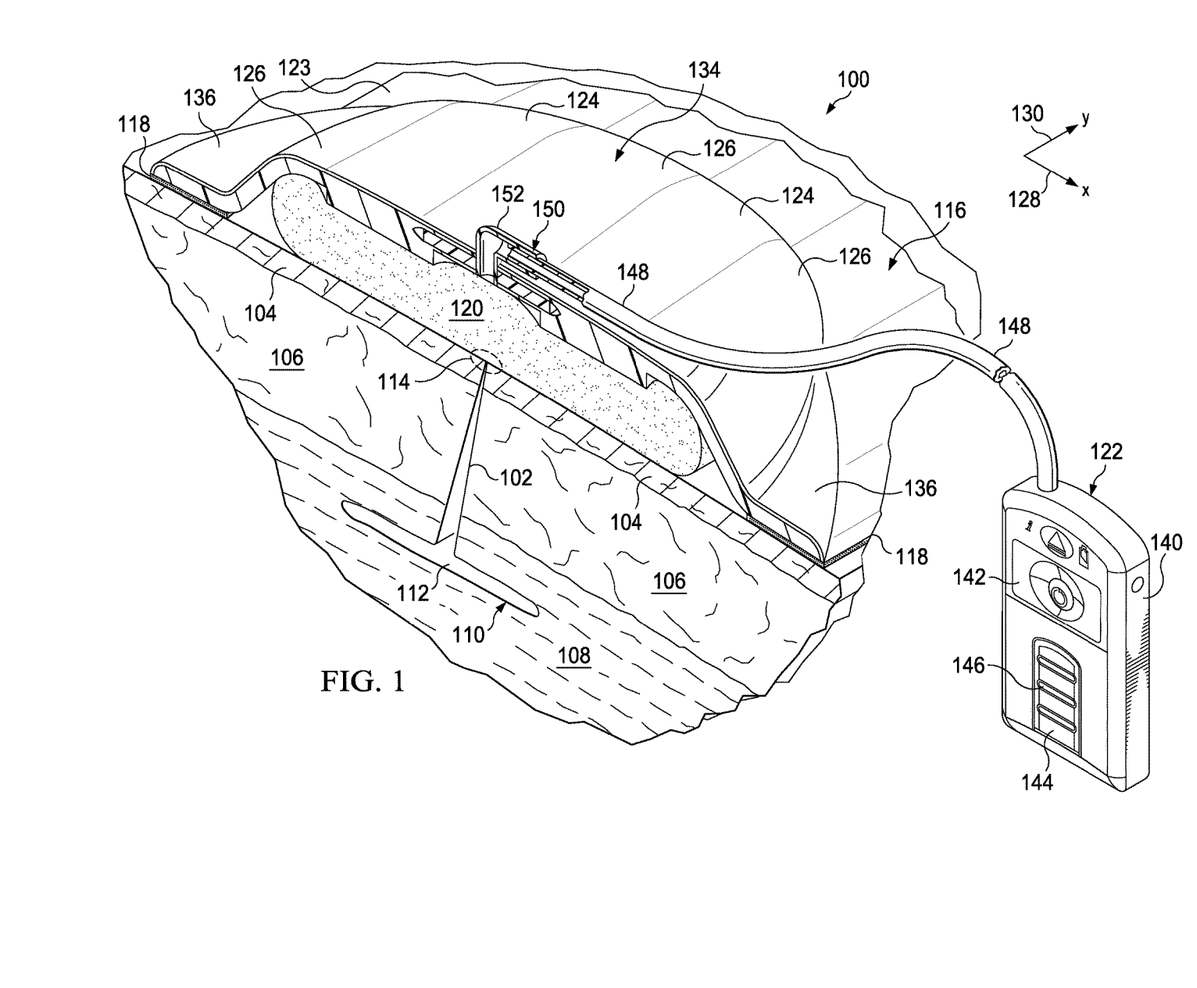
FIG. 1 is a schematic, perspective view with a portion shown in cross-section of an illustrative embodiment of a reduced-pressure wound treatment system.

The reduced-pressure treatment system 100 is shown in a peri-incisional region around incision 102, which is through epidermis 104, or skin, and dermis 106 and reaching into hypodermis, or subcutaneous tissue 108. The subcutaneous tissue 108 may include numerous tissue types such as fatty tissue or muscle. An undermined subcutaneous tissue site 110 is shown extending out from incision 102 and includes, in this instance, subcutaneous defect or void 112. The undermined subcutaneous tissue 110 is often caused by surgical procedures, such as liposuction. The undermined subcutaneous tissue 110 may include voids, such as void 112, open spaces, and various defects that can be troublesome for a number of reasons, such as allowing fluids to build that may result in edema. The term "fluid" as used herein generally refers to gas or liquid, but may also include any other flowable material, including but not limited to gels, colloids, and foams.

The incision 102 may be closed using any mechanical closing means such as staples, sutures, or adhesive, but is shown in this illustrative embodiment with a suture 114. The illustrative embodiment shows the reduced-pressure treatment system 100 in use in a peri-incisional region. It will be appreciated that the reduced-pressure treatment system 100 may be used to treat undermined subcutaneous tissue 110 where there is no corresponding incision or any other kind of tissue site.

The reduced-pressure treatment system 100 generally includes a drape, or wound drape 116, a manifold 120, and a reduced-pressure subsystem 122. The reduced-pressure treatment system 100 may also include gripping member 118. The wound drape 116 is generally formed from a sheet, or flexible sheet 123, and includes one or more first isotropic zones 124 and one or more second isotropic zones 126. Each zone is typically a region, or area, that makes up at least one half percent of the wound drape 116. The first and second isotropic zones 124, 126 are configured to provide the flexible sheet 123 with anisotropic properties. As such, the flexible sheet 123 may help the wound drape 116 primarily stretch in a given direction. Stated another way, the flexible sheet 123 can stretch more along one direction than along another, different direction. As used herein, stretching may include elastic and inelastic deformation. These anisotropic properties may be accomplished in a variety of ways, and several illustrative embodiments will be discussed further below beginning with the use of different thicknesses.

In the illustrative embodiment of FIGS. 1-3B, the first isotropic zones 124 have a first thickness ($t_1$) of drape material and the second isotropic zones 126 have a second thickness ($t_2$) of drape material, and the thickness of each first isotropic zone 124 is greater than the thickness of each second isotropic zone 126 ($t_1 > t_2$). Because the thickness ($t_1$) of each first isotropic zone 124 is greater than the thickness ($t_2$) of each second isotropic zone 126, the flexible sheet 123 is provided with anisotropic properties whereby the flexible sheet 123 stretches more in the direction of a first (x) axis 128 than in the direction of a second (y) axis 130 under equal force in the direction of each axis. In one illustrative embodiment, the first thickness ($t_1$) is greater than or equal to one hundred five percent (105%) of the second thickness ($t_2$), i.e., $t_1 \geq 105\% \, t_2$. In another illustrative embodiment, the first thickness ($t_1$) is greater than or equal to one hundred ten percent (110%) of the second thickness ($t_2$), i.e., $t_1 \geq 110\% \, t_2$. Other relationships between the first thickness ($t_1$) and the second thickness ($t_2$) are possible.

Figure 2:
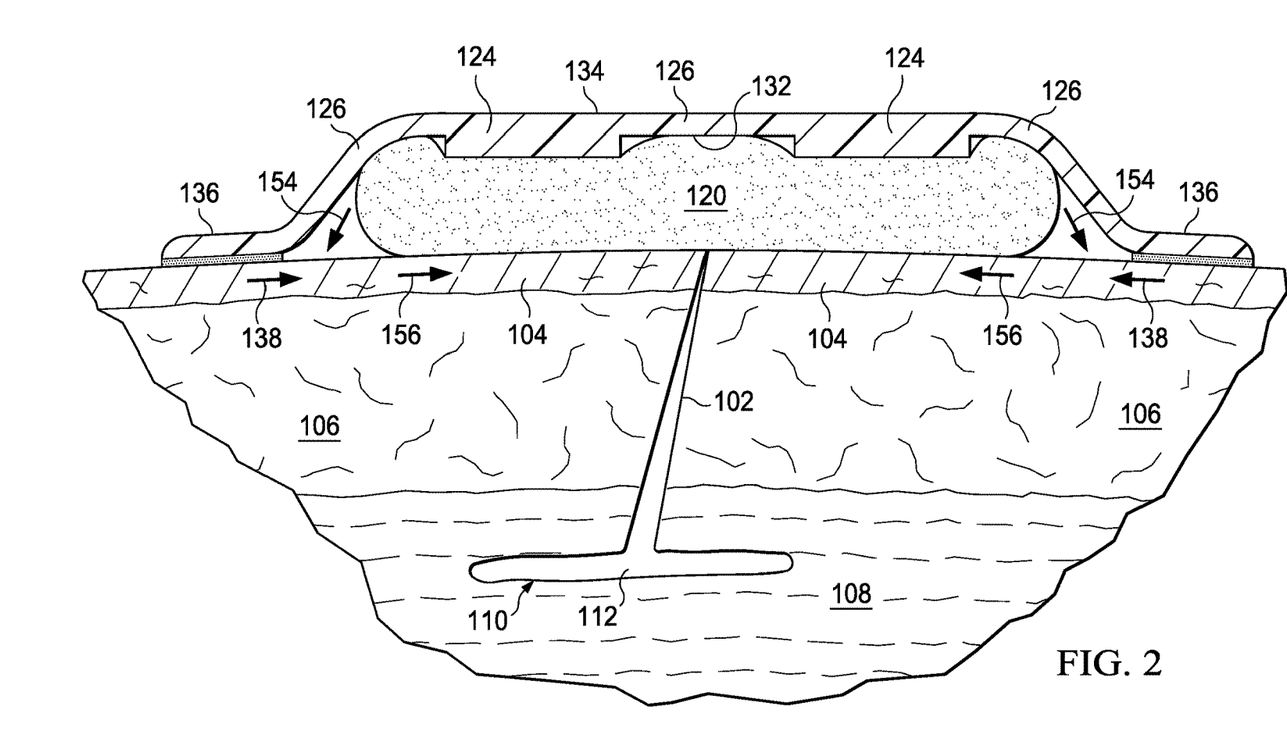
FIG. 2 is a schematic, cross-sectional view of a portion of the reduced-pressure wound treatment system of FIG. 1.
Figure 3A:
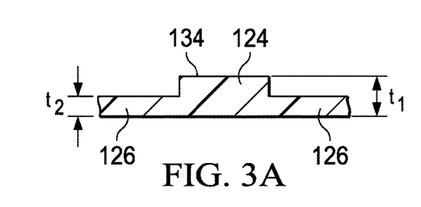
FIG. 3A is a schematic, cross-sectional view of a first isotropic zone and a second isotropic zone of an illustrative embodiment of a wound drape.
Figure 3B:
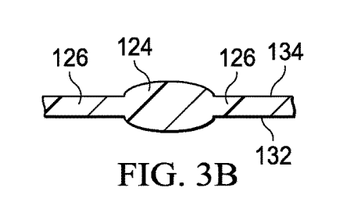
FIG. 3B is a schematic, cross-sectional view of a first isotropic zone of another illustrative embodiment of a wound drape.

Indeed, by selecting appropriate thicknesses, a user may selectively control the rate or force with which the flexible sheet 123 attempts to return to its original size after it is stretched and adhered to a patient. Thus, the rate of the translation and/or approximation of tissue may be regulated. Regulating the translation and/or approximation of tissue may serve to minimize skin complications, such as blisters, hyper-pigmentation, etc., as well as to assist in closing the incision 102. Additionally, the thicker first isotropic zones 124 may be capable of providing a compressive force that may be realized in the subcutaneous tissue 108 and may be beneficial in treating the undermined subcutaneous tissue 110 and eliminating voids 112 or the like. As shown in FIG. 2, the first isotropic zones 124 may project inwardly from a skin-facing surface 132. As shown in FIG. 3A, the first isotropic zones 124 may project outwardly from a first surface 134 of the flexible sheet 123. As shown in FIG. 3B, the first isotropic zones 124 may project from both of the skin-facing surface 132 and first surface 134. It will be appreciated that any number of isotropic zones may be employed as part of flexible sheet 123. Moreover, while the isotropic zones 124, 126 are shown as substantially parallel with one another, it will be appreciated that the zones 124, 126 may be arranged with different orientations with respect to one another. While two thicknesses ($t_1$ and $t_2$) are shown for two zones 124, 126, it should be understood that many zones having varying thicknesses may be used to achieve the anisotropic properties.

The wound drape 116 may be sized so that it overlaps the incision 102 and/or undermined subcutaneous tissue 110 in such a manner that a drape extension 136 extends beyond the periphery of the incision 102 and/or undermined subcutaneous tissue 110. The wound drape 116 may be formed from any suitable material, such as an impermeable or semi-permeable elastomeric material. "Elastomeric" means having the properties of an elastomer and generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Sealing drape materials may include a silicone material, 3M Tegaderm® drape material, acrylic drape material such as one available from Avery Dennison Corporation of Pasadena, Calif., or an incise drape material. However, it will be appreciated that the wound drape 116 may be formed from any suitable material. In addition, the first and second isotropic zones 124, 126 may be formed from the same drape material or from different drape materials. The isotropic zones 124, 126 may be formed via a co-extrusion process, a molding process, or any other suitable forming process. The varying thicknesses may be achieved by coupling two or more portions of drape material that are not co-extensive. Optionally, the drape material may also include one or more suitable bioactive elements, including, but not limited to, antimicrobial compounds or any other suitable bioactive element(s).

The gripping member 118 may be coupled to the wound drape 116. The gripping member 118 is operable to couple the wound drape 116 to a patient's epidermis 104. Also, the gripping member 118 may also be operable to transmit a closing force generated by drape 116 as the drape 116 attempts to return to the drape's 116 original size after being stretched and adhered to a patient (the transmitted force is illustrated as force vectors 138 in FIG. 2). Additionally, the wound drape 116 and gripping member 118 work together to form a fluid seal over the patient's epidermis 104. "Fluid seal," or "seal," means a seal adequate to hold reduced pressure at the desired site given the particular reduced-pressure subsystem involved. The gripping member 118 may be any material suitable for coupling the drape 116 to a patient's epidermis 104, transmitting a closing force to the patient's epidermis 104, and/or assist in forming a fluid seal over the patient's epidermis 104. For example, the gripping member 118 may be a pressure-sensitive adhesive, heat-activated adhesive, sealing tape, double-sided sealing tape, paste, hydrocolloid, hydrogel, hooks, sutures, etc.

In the illustrative embodiment, the gripping member 118 is an adhesive layer coupled to the skin-facing surface of the drape extension 136; however, it will be appreciated that gripping member 118 may span the entire width of the drape 116. Alternatively, the gripping member 118 may be applied to only a selected portion of the wound drape 116, such as the first or second isotropic zones 124, 126. The gripping member 118 may be formed as a layer or a pattern distributed on the wound drape 116. Alternatively, in the case of sealing tape, the gripping member 118 may be applied over the entire first surface 134 of the wound drape 116 or over the first surface of the drape extension 136.

The manifold 120 is positionable between the skin-facing surface 132 of the wound drape 116 and the tissue site, e.g., incision 102, within a wound bed, or over an intact portion of the epidermis 104. The term "manifold" as used herein generally refers to a substance or structure that is provided to assist in applying reduced pressure to, delivering fluids to, or removing fluids from a tissue site, e.g., incision 102. The manifold 120 may be made of many different materials.

In one illustrative embodiment, the manifold 120 is made from a porous and permeable foam-like material and, more particularly, a reticulated, open-cell polyurethane or polyether foam that allows good permeability of wound fluids while under a reduced pressure. One such foam material that may be used is the V.A.C.® GranuFoam® material available from Kinetic Concepts, Inc. (KCI) of San Antonio, Tex. Any material or combination of materials may be used for the manifold material provided that the manifold material is operable to distribute the reduced pressure. The manifold 120 typically includes a plurality of flow channels or pathways that distribute fluids provided to and removed from the area of tissue around the manifold 120. The flow channels may be interconnected. Examples of manifolds may include, without limitation, devices that have structural elements arranged to form flow channels, cellular foam, such as open-cell foams, textiles, porous tissue collections, and liquids, gels, and foams that include, or cure to include, flow channels. The manifold material may also be a combination or layering of materials. For example, a first manifold layer of hydrophilic foam may be disposed adjacent to a second manifold layer of hydrophobic foam to form the manifold material.

The reticulated pores of the GranuFoam® material, that are in the range from about 400 to 600 microns, are helpful in carrying out the manifold function, but other materials may be used. The manifold material may be a reticulated foam that is later felted to a thickness of about ⅓ of the manifold material's original thickness. Among the many possible materials, the following may be used: Granu-Foam® material or a Foamex® technical foam (www.foamex.com). In some instances it may be desirable to add ionic silver to the foam in a microbonding process or to add other substances to the manifold material such as antimicrobial agents. The manifold material may be isotropic or anisotropic. In addition, the manifold material may be a bio-absorbable or bio-includable material.

The manifold 120 may be coupled to the wound drape 116. As used herein, the term "coupled" includes coupling via a separate object and includes direct coupling. The term "coupled" also encompasses two or more components that are continuous with one another by virtue of each of the components being formed from the same piece of material. Also, the term "coupled" may include chemical, such as via a chemical bond, mechanical, thermal, or electrical coupling. Fluid coupling means that fluid is in communication between the designated parts or locations.

The wound drape 116 and manifold 120 may be coupled using adhesives such as an acrylic adhesive, silicone adhesive, hydrogel, hydrocolloid, etc. Alternatively, the wound drape 116 and manifold 120 may be bonded by heat bonding, ultrasonic bonding, and radio frequency bonding, etc. The coupling may occur in patterns. In addition, structure may be added to the bond to make the wound drape 116 behave even more anisotropically in a desired direction.

The reduced-pressure subsystem 122 includes a reduced-pressure source 140, which can take many different forms. The reduced-pressure source 140 provides reduced pressure as a part of the reduced-pressure treatment system 100. As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. Reduced pressure may initially generate fluid flow in the manifold 120, a reduced-pressure conduit, or conduit 148, and proximate the tissue site, e.g., incision 102. As the hydrostatic pressure around the tissue site approaches the desired reduced pressure, the flow may subside, and the reduced pressure may be maintained. Unless otherwise indicated, values of pressure stated herein are gauge pressures. The reduced pressure delivered may be static, dynamic (patterned or random) and may be delivered continuously or intermittently. The operable range of reduced pressure may vary widely as needed, but would typically be between −5 mm Hg and −500 mm Hg. Various sources of reduced pressure may be utilized such as V.A.C.® therapy unit, which is available from Kinetic Concepts, Inc. of San Antonio, Tex., or a wall suction unit. The reduced-pressure source 140 could also be supplied by a portable mechanical means, such as a piston in a tube, depending on how much leakage there is with the fluid seal between the wound drape 123 and the epidermis 104.

In the illustrative embodiment, the reduced-pressure source 140 is shown having a battery compartment 142 and a canister region 144 with windows 146 providing a visual indication of the level of fluid within canister 144. An interposed membrane filter, such as hydrophobic or oleophobic filter, may be interspersed between reduced-pressure conduit 148 and the reduced-pressure source 140.

The reduced pressure developed by the reduced-pressure source 140 is delivered through the reduced-pressure conduit 148 to a reduced-pressure interface 150, or interface 150, which may be an elbow port 152. In one illustrative embodiment, the elbow port 152 is a TRAC® technology port available from Kinetic Concepts, Inc. of San Antonio, Tex. The reduced-pressure interface 150 allows the reduced pressure to be delivered to the wound drape 116 and realized within an interior portion of wound drape 116 and the manifold 120. In this illustrative embodiment, the elbow port 152 extends through the flexible sheet 123 to the manifold 120, but numerous arrangements are possible.

In operation, the manifold 120 may be placed proximate the tissue site, e.g., incision 102 and/or undermined subcutaneous tissue 110. The wound drape 116 may be placed over the manifold 120 such that the drape extension 136 of the wound drape 116 extends beyond the incision 102 and/or undermined subcutaneous tissue 110. The drape 116 may be stretched to a desired length. As previously mentioned, while stretching the drape 116, the second isotropic zones 126 may stretch more than the first isotropic zones 124. The drape extension 136 may then be secured to the patient's epidermis 104 by a gripping member 118 in order to form a fluid seal between the drape 116 and the patient's epidermis 104. In some instances, the gripping member 118 may also serve to transmit a closing force to the patient's epidermis 104 generated by the drape 116 as the drape 116 attempts to contract while coupled to the patient's epidermis 104. The reduced-pressure interface 150 is then applied, if not already installed, and the reduced-pressure conduit 148 is fluidly coupled to the reduced-pressure interface 150. The reduced-pressure conduit 148 is also fluidly coupled to the reduced-pressure source 140. The reduced-pressure source 140 may then be activated such that a reduced pressure is delivered to the interior of the wound drape 116 and manifold 120.

As the reduced pressure is delivered, the manifold 120 may compress and contract laterally to form a semi-rigid substrate. A number of beneficial forces and actions may take place. The reduced pressure is transmitted further still through the manifold 120 so that the reduced pressure is experienced at the patient's epidermis 104 and at the incision 102. At least at the early stages of the healing process, the reduced pressure may also be realized through the incision 102 and into the subcutaneous tissue 108. The reduced pressure helps close defects, such as a subcutaneous void 112, and generally provides stability to the area. The reduced pressure delivered to the drape 116 also develops a compressive force, as suggested by arrows 154, which again may provide stability and therapy. The compressive force, as suggested by arrows 154, is more than just at the level of the epidermis 104; the compressive force may extend down deeper and may be experienced at the level of subcutaneous tissue 108.

Further, as the wound drape 116 and manifold 120 laterally contract under the influence of the reduced pressure, an inward force, as suggested by arrows 156, may develop that helps hold an additional closing force on the incision 102 and may generally provide additional stability to the wound. Thus, the inward force, represented by arrows 156, from the reduced pressure and the closing force, represented by arrows 138, generated by the contraction of the drape 116 may act together to assist in helping to close the incision 102 and/or maintaining the incision 102 in a substantially closed position. At the same time, the reduced pressure delivered to and through the manifold 120 helps to remove any exudates and other fluids from the incision 102. All of these actions may improve healing of the tissue site, e.g., incision 102.

It may be desirable to apply the reduced-pressure treatment system 100 in the operating room and allow the system 100 to remain on the patient until adequate healing has taken place. In this regard, it may be desirable to form the wound drape 116, manifold 120, and any other layers from transparent materials to allow the healthcare provider to gain visual cues about the healing of the tissue site, e.g., incision 102, without having to remove the drape 116. Moreover, it should be appreciated that the reduced-pressure treatment system 100 may be used as a primary wound-closing treatment or as an intermediate step of a wound-closing treatment protocol. Furthermore, it will be appreciated that the wound drape 116 may be used without the manifold 120 and/or reduced pressure sub-system 122. Moreover, it should be appreciated that the wound-drape 116 may be beneficial as a stand-alone dressing that is capable of delivering a closing force and/or a compressive force to an incision 102 and/or undermined subcutaneous tissue 110.

Figure 4A:
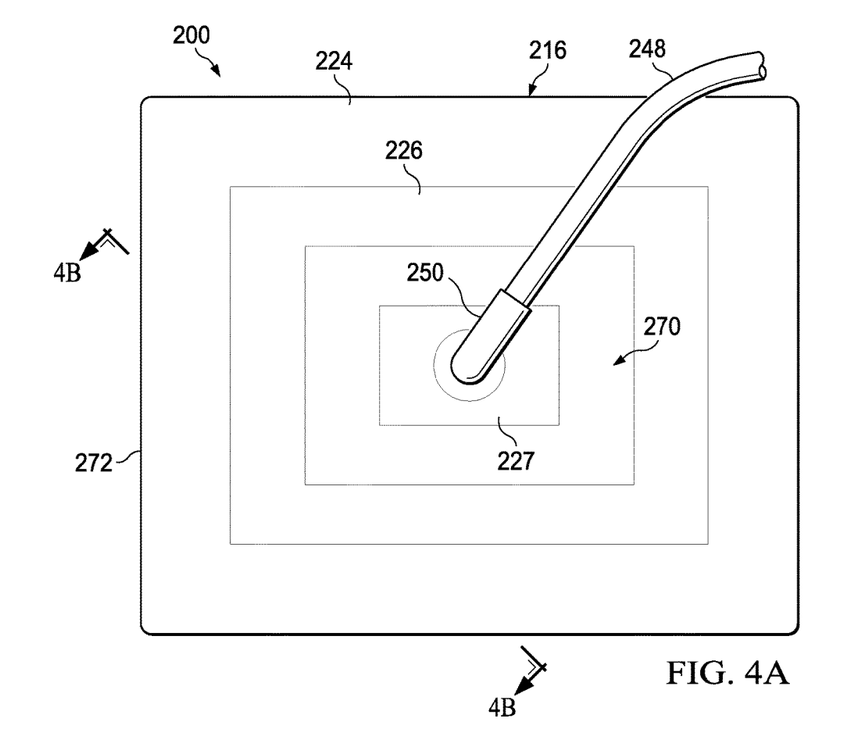
FIG. 4A is a schematic, top view of an illustrative embodiment of a portion of a reduced-pressure wound treatment system.
Figure 4B:
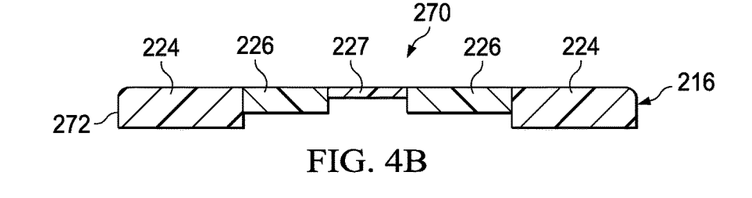
FIG. 4B is a schematic, cross-sectional view of the reduced-pressure wound treatment system of FIG. 4A taken along line 4B-4B in FIG. 4A.

Referring to FIGS. 4A and 4B, a second illustrative embodiment of a portion of a reduced-pressure treatment system 200 is shown for treating a tissue site, such as an incision, undermined subcutaneous tissue, or other wound. The reduced-pressure treatment system 200 is analogous in most respects to the reduced-pressure treatment system 100 of FIGS. 1-3B and a correlation of parts is generally indicated in this embodiment by indexing the numerals in FIGS. 1-3B by 100. While presented with a reduced-pressure interface 250 and conduit 248 for connection to a reduced pressure subsystem (not shown), it will be appreciated that the drape 216 may be used as a stand-alone dressing as well.

The wound drape 216 includes a first isotropic zone 224, a second isotropic zone 226, and a third isotropic zone 227. The first isotropic zone 224 is thicker than the second isotropic zone 226, and the second isotropic zone 226 is thicker than the third isotropic zone 227. In this embodiment, isotropic regions are created so that with equal force applied across the drape 216, the region defined by first isotropic zone 224 will stretch less than the region defined by second isotropic zone 226. It will be appreciated that the isotropic zones 224, 226 227 may be of any suitable thickness relative to one another (e.g., the third zone 227 may be the thickest, etc.). Moreover, while the present embodiment shows three isotropic zones, it will be appreciated that any number of isotropic zones may be employed. The isotropic zones 224, 226, 227 are concentric with one another and are annular-square shaped areas when viewed in plan view. However, it will be appreciated that the isotropic zones 224, 226, 227 do not necessarily need to be concentric with one another. Additionally, it will be appreciated that each isotropic zone 224, 226, 227 may have any suitable shape when viewed in plan, including but not limited to circular, elliptical, triangular, rectangular, octagonal, etc.

In another illustrative embodiment, the wound drape 216 has defined isotropic zones 224, 226, 227, but the transitions between zones may be gradual. In another illustrative embodiment, the wound drape 216 is tapered such that the thickness of the wound drape 216 either gradually increases or gradually decreases from an inner portion 270 to the edge 272 of the wound drape 216. Thus, the modulus of elasticity of the wound drape 216 evenly and gradually changes across the length of the wound drape 216. In FIGS. 4A and 4B, the inner portion 270 is the substantial center of the wound drape 216, although the inner portion 270 may be located anywhere inside the edges 272 of the wound drape 216

In one example, the wound drape 216 can be thickest at the edge 272 and gradually become thinner towards the inner portion 270 such that the center 270 is the thinnest portion of the wound drape 216. The shape of the resulting cavity may approximate a cone, including a frustoconical shape. Conversely, the wound drape 216 can be thinnest at the periphery 272 and gradually become thicker towards the center 270 such that the center 270 is the thickest portion of the wound drape 216. Any of the illustrative embodiments of the wound drape described herein, including those having substantially parallel isotropic zones, are able to have even and gradual, or tapered, changes in thickness or elastic modulus instead of having clearly defined isotropic zones. In an embodiment in which the isotropic zones are substantially parallel to one another, the inner portion 270 may extend from one edge of the wound drape 216 to an opposing edge. Tapering of the wound drape 216 can help to relieve strain at a tissue site to which the wound drape 216 is applied, and can alleviate skin irritation (e.g., blisters). Such tapering can also offer desirable stretching characteristics to facilitate wound healing.

Figure 5A:
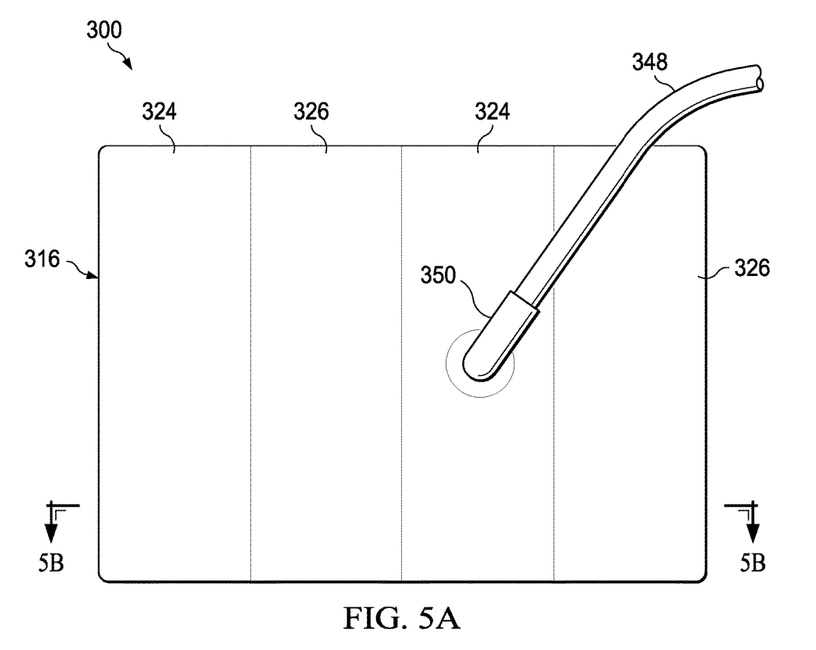
FIG. 5A is a schematic, top view of an illustrative embodiment of a portion of a reduced-pressure wound treatment system.
Figure 5B:
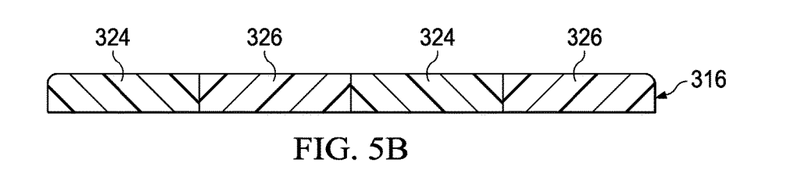
FIG. 5B is a schematic, cross-sectional view of the reduced-pressure wound treatment system of FIG. 5A taken along line 5B-5B in FIG. 5A.

Referring now to FIGS. 5A and 5B, another illustrative embodiment of a portion of a reduced-pressure treatment system 300 for treating a tissue site on a patient is shown. The reduced-pressure treatment system 300 is generally analogous in most respects to that of the reduced-pressure treatment system 100 of FIGS. 1-3B and a correlation of parts is generally indicated in this embodiment by indexing the reference numerals of FIGS. 1-3B by 200. While presented with a reduced-pressure interface 350 and conduit 348 for connection to a reduced pressure subsystem (not shown), it will be appreciated that the wound drape 316 may be used as a stand-alone dressing.

The wound drape 316 includes first isotropic zones 324 and second isotropic zones 326. The first isotropic zones 324 are formed from a material having a first modulus of elasticity ($\lambda_1$) and the second isotropic zones 326 are formed from a material having a second modulus of elasticity ($\lambda_2$). In the illustrative embodiment, the first modulus of elasticity is greater than the second modulus of elasticity ($\lambda_1 > \lambda_2$) such that the second isotropic zones 326 stretch more than the first isotropic zones 324 when the wound drape 316 is stretched. The wound drape 316 stretches primarily in one direction versus other directions. For example, in one embodiment, the wound drape 316 may primarily stretch in a direction substantially perpendicular to one or more elongated isotropic zones 324, 326.

By selecting the appropriate modulus of elasticity for each isotropic zone 324, 326, a user may selectively control the rate or force with which the wound drape 316 attempts to return to the drape's 316 original size after being stretched and adhered to a patient. Thus, the rate of or force related to the translation and/or approximation of tissue may be regulated. While the illustrative embodiment shows two of each isotropic zones 324, 326, it will be appreciated that any suitable number of isotropic zones may be employed. Additionally, it will be appreciated that the wound drape 316 may include any number of isotropic zones of varying moduli of elasticities or even be constructed of continuously variable elasticity across at least one of the wound drape surfaces. In one embodiment, the isotropic zones nearest the edge of the wound drape 316 have the lowest modulus of elasticity relative to other isotropic zones of the wound drape 316.

In another embodiment, one or more isotropic zones may have a modulus of elasticity equal to or substantially similar to that of the tissue at or near the tissue site to which the zones are attached. As a few non-limiting examples, the modulus of elasticity of the isotropic zone may be within twenty percent of the modulus of elasticity of the patient's epidermis or within ten percent of the modulus of elasticity of the patient's skin or within five percent of the modulus of elasticity of the patient's skin. Coordinating the modulus of elasticity of the isotropic zones with the modulus of elasticity of tissue at the tissue site may minimize stress applied to the tissue or stress-shielding and promote healing and minimize scarring. Furthermore, it will be appreciated that the isotropic zones 324, 326 may be configured such that they are annular shaped when viewed in plan view and the isotropic zones 324, 326 may or may not be arranged such that the isotropic zones 324, 326 are concentric with one another. In addition, while the isotropic zones 324, 326 are shown having substantially similar thicknesses, it will be appreciated that the isotropic zones 324, 326 may be of different thicknesses. Thus, the anisotropicity of the wound drape 316 may be achieved by combining different zones having different moduli of elasticities as well as different thicknesses. Also, the thickness and moduli of the wound drape 316 may evenly and gradually taper along one or more directions of the wound drape 316 or a portion thereof. Moreover, while the isotropic zones 324, 326 are shown as substantially parallel with one another, it will be appreciated that the isotropic zones 324, 326 may have any suitable arrangement relative to one another.

Figure 6A:
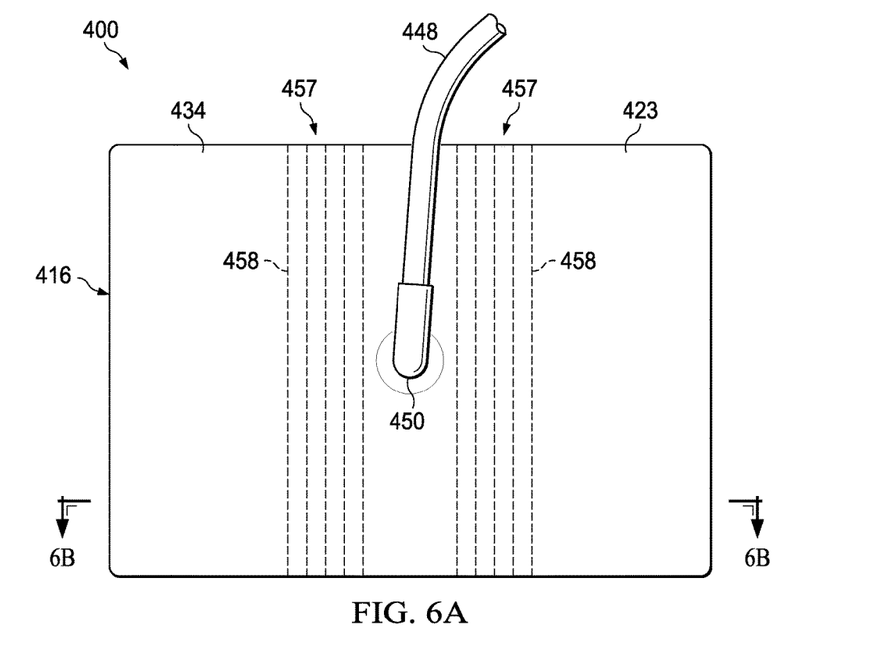
FIG. 6A is a schematic, top view of an illustrative embodiment of a portion of a reduced-pressure wound treatment system.
Figure 6B:
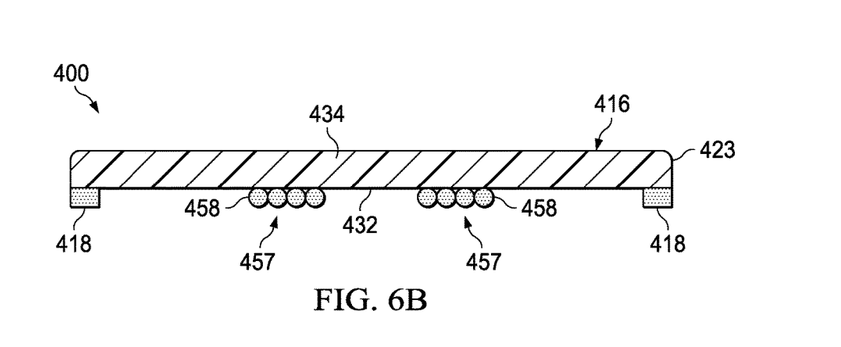
FIG. 6B is a schematic, cross-sectional view of the reduced-pressure wound treatment system of FIG. 6A taken along line 6B-6B in FIG. 6A.

Referring now to FIGS. 6A-6B, another illustrative embodiment of a portion of a reduced-pressure treatment system 400 for treating a tissue site on a patient is shown. The reduced-pressure treatment system 400 generally includes a wound drape 416 and one or more gripping members 418. A reduced-pressure interface 450 and conduit 448 may be coupled to the wound drape 416 for connection to a reduced-pressure source (not shown) such that a reduced pressure may be delivered to the tissue site. It should, however, be appreciated that the wound drape 416 may be used as a stand alone dressing.

The wound drape 416 is generally formed from a flexible sheet 423 having one or more anisotropic members 457 coupled thereto. The anisotropic members 457 are configured to provide the wound drape 416 with anisotropic properties. In this illustrative, non-limiting example, the wound drape 416 is operable to stretch in the areas between the anisotropic members 457, but stretches minimally or not at all in the direction of the longitudinal axis of the anisotropic members 457. In the illustrative embodiment, the anisotropic members 457 comprise a plurality of filaments 458. The filaments 458 may be formed from any suitable material, including but not limited to, polymer, fabric, metal, composite, elastomer, etc. In addition, the filaments 458 may be arranged such that they are substantially parallel with one another. It will, however, be appreciated that the filaments 458 may have any suitable arrangement capable of providing the drape 416 with anisotropic properties; for example, the filaments may be in a "thatched" arrangement, a substantially random arrangement, etc. The filaments 458 may also be formed from additional drape material in some illustrative embodiments.

The filaments 458 are coupled to the flexible sheet 423 by any suitable means, including but not limited to, adhesive, mechanical fasteners, bonding, sonic welding, etc. The filaments 458 may be coupled to either the skin-facing surface 432 or the first surface 434 of the flexible sheet 423. Additionally, the filaments 458 may be formed with the flexible sheet 423, through a process such as co-extrusion, whereby the filaments 458 are substantially co-planar with the flexible sheet 423. Also, while illustrative embodiment shows two anisotropic members 457, it will be appreciated that any number of anisotropic members 457 may be employed. Further, while the anisotropic members 457 are shown as substantially parallel with one another, it will be appreciated that the anisotropic members 457 may have any suitable arrangement relative to one another. Moreover, it will be appreciated that the anisotropic members 457 may be arranged such that they are annular in shape when viewed in plan and they may or may not be arranged such that they are concentric with one another.

While the anisotropic members 457 are shown as comprising a plurality of filaments 458 in this illustrative embodiment, it will be appreciated that the anisotropic members 457 may have any suitable configuration and arrangement. For example, the anisotropic members may include adhesive layers coupled to the flexible sheet 423. The adhesive layers may or may not be patterned. Other possible configurations and arrangements for the anisotropic members are possible. In addition, the gripping member 418 is the same or similar to gripping member 118 of the reduced-pressure treatment system 100 of FIGS. 1-3B. In the illustrative embodiment, the gripping member 418 may be coupled to the skin-facing surface 432 of the flexible sheet 423. The gripping member 418 may span the entire width of the flexible sheet 423 and overlay the filaments 458 or may be located near the ends of the flexible sheet 423 as shown in FIG. 6B.

Figure 7A:
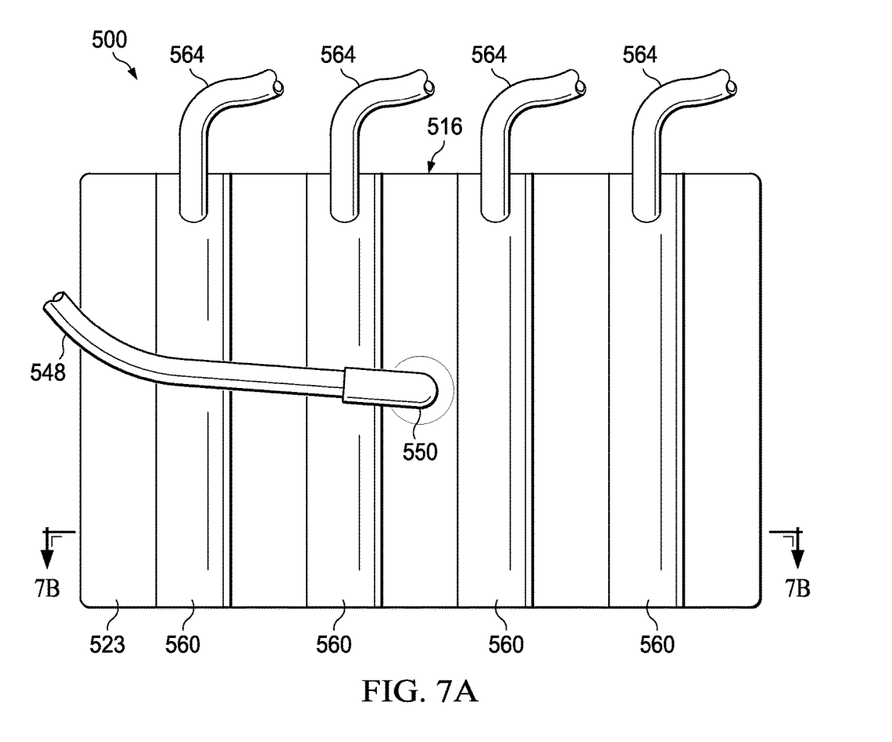
FIG. 7A is a schematic, top view of an illustrative embodiment of a reduced-pressure wound treatment system.
Figure 7B:
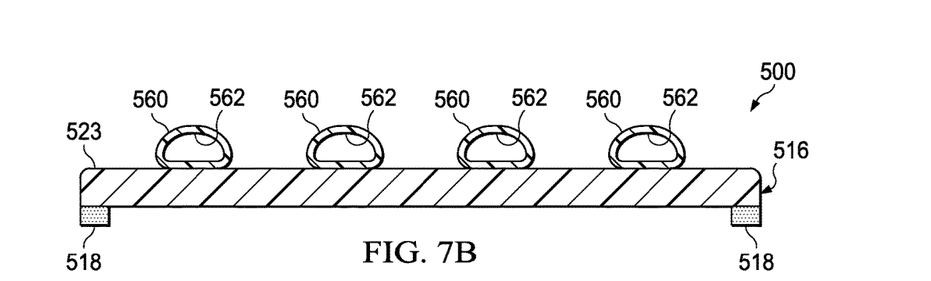
FIG. 7B is a schematic, cross-sectional view of the reduced-pressure wound treatment system of FIG. 7A taken along line 7B-7B in FIG. 7A.

Referring now to FIGS. 7A and 7B, another illustrative embodiment of a portion of a reduced-pressure treatment system 500 for treating a tissue site on a patient is shown. The reduced-pressure treatment system 500 generally includes a wound drape 516 and one or more gripping members 518. A reduced-pressure interface 550 and conduit 548 may be coupled to the wound drape 516 for fluidly coupling to a reduced-pressure source (not shown) such that a reduced pressure may be delivered to the tissue site. It will, however, be appreciated that the wound drape 516 may be used as a stand alone dressing.

The wound drape 516 is generally formed from a flexible sheet 523 having one or more fluidly inflatable bladders 560. Each fluidly inflatable bladder 560 includes an interior chamber 562 for receiving a fluid to inflate the fluidly inflatable bladder 560. Fluid is supplied to each interior chamber 562 by a corresponding fluid supply tube or conduit 564; however, it will be appreciated that a single fluid supply tube may be configured to deliver fluid to each bladder via passageways (not shown) that interconnect the fluidly inflatable bladders 560. The fluid may be delivered to the interior chambers 562 from a fluid control means (not shown). The fluid control means may be any suitable device capable of storing and selectively delivering fluid through the tube(s) 564 to the interior chambers 562. An illustrative fluid control means includes, but is not limited to, a pump, cylinder, reservoir, etc. with corresponding control mechanisms, including, but not limited to, valves, clamps, regulators, etc. The fluidly inflatable bladders 560 may be inflated with any suitable material, including but not limited to, air, water, saline, a gel, a foam, etc.

The fluidly inflatable bladders 560 are configured to provide the wound drape 516 with anisotropic properties. In the illustrative embodiment, the fluidly inflatable bladders 560 provide the wound drape 516 with anisotropic properties by virtue of the rigidity they supply such that the wound drape 516 functionally behaves similarly to that of FIG. 1-3B whereby the flexible sheet 523 stretches more in the area between the bladders 560 when a stretching force is applied thereto. Furthermore, it will be appreciated that by controlling the volume of fluid delivered through the fluid supply tubes 564, it may be possible to control the anisotropic properties of the wound drape 516. For example, as the fluid is delivered to the fluidly inflatable bladders 560, the anisotropicity of the drape 516 may increase. The fluid delivered through the tube 564 may also be varied to provide a dynamic anisotropic sheet. A controller may be provided to control the fluid control means in response to conditions at the wound site. Moreover, it will be appreciated that inflating the fluidly inflatable bladders 560 prior to stretching and applying the wound drape 516 may further enhance the anisotropic behavior. In addition, once the fluidly inflatable bladders 560 are inflated, they may be operable to provide a compressive force that may be realized in subcutaneous tissue and that may be beneficial in treating the undermined subcutaneous tissue and eliminating voids or the like.

The fluidly inflatable bladders 560 may be coupled to the flexible sheet 523 by any suitable means, including but not limited to adhesive, mechanical fasteners, bonding, sonic welding, etc. The fluidly inflatable bladders 560 may be coupled to either the skin-facing surface 532 or first surface 534 of the flexible sheet 523. Additionally, the fluidly inflatable bladders 560 may be formed to be substantially co-planar with the flexible sheet 523 prior to their inflation. While the illustrative embodiment shows four fluidly inflatable bladders 560, it will be appreciated that any number of bladders 560 may be employed. Further, while the fluidly inflatable bladders 560 are shown as substantially parallel with one another, it will be appreciated that the fluidly inflatable bladders 560 may have any suitable arrangement relative to one another. Moreover, it will be appreciated that the fluidly inflatable bladders 560 may be arranged such that the fluidly inflatable bladders 560 are annular shaped when viewed in plan and the fluidly inflatable bladders 560 may or may not be arranged such that the fluidly inflatable bladders 560 are concentric with one another.

In addition, the gripping member 518 is the same or similar to the gripping member 118 of the reduced-pressure treatment system 100 of FIGS. 1-3B. In the illustrative embodiment, the gripping member 518 may be coupled to the skin-facing surface 532 of the flexible sheet 523. The gripping member 518 may span the entire width of the flexible sheet 523 and overlay the filaments 558 or may be located near the ends of the flexible sheet 523.

In one illustrative embodiment, the fluidly inflatable bladders 560 are inflated with positive pressure through fluid supply tubes 564 and as reduced pressure is supplied to the reduced-pressure interface 550, the inflatable bladders 560 press against the patient's epidermis with a compressive force. As reduced pressure increases, the inflatable bladders 560 are drawn toward the reduced-pressure interface 550 and thereby create a closing force. The closing force is realized at the epidermis and may be realized at deeper levels, e.g., the dermis.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in a connection to any one embodiment may also be applicable to any other embodiment.

The invention claimed is:

1. A wound drape comprising:
   a flexible sheet formed of an impermeable elastomeric material and having an inner portion and an edge, the thickness of the flexible sheet gradually changes from the inner portion to the edge to provide the flexible sheet with anisotropic stretching properties such that the flexible sheet stretches more in a first direction than in a second direction; and
   an adhesive coupled to the flexible sheet, wherein the adhesive is operable to couple the wound drape to a patient's epidermis.

2. The wound drape of claim 1, wherein the inner portion is the substantial center of the wound drape.

3. The wound drape of claim 1, wherein the modulus of elasticity of the flexible sheet gradually changes from the inner portion to the edge.

4. The wound drape of claim 1, wherein the thickness of the flexible sheet gradually increases from the inner portion to the edge such that the edge is thicker than the inner portion.

5. The wound drape of claim 1, wherein the thickness of the flexible sheet gradually decreases from the inner portion to the edge such that the edge is thinner than the inner portion.

6. The wound drape of claim 1, wherein the adhesive is operable to transmit a closing force generated by the wound drape to the patient's epidermis.

7. The wound drape of claim 1, wherein the wound drape and the adhesive are operable to form a fluid seal over a tissue site on the patient.

8. The wound drape of claim 7, wherein the fluid seal is adapted to hold reduced pressure at the tissue site.

9. The wound drape of claim 1, wherein the wound drape and the adhesive are operable to form a fluid seal over a manifold at a tissue site on the patient, the manifold configured to distribute a reduced pressure to a tissue site on the patient.

10. The wound drape of claim 1, wherein the flexible sheet is adapted to be coupled to a reduced-pressure source for treating a tissue site on the patient with reduced pressure.

11. The wound drape of claim 1, wherein the flexible sheet is comprised of transparent material.

12. The wound drape of claim 1 further comprising a manifold coupled to the flexible sheet, the manifold configured to distribute a reduced pressure to a tissue site on the patient.

13. The wound drape of claim 12, wherein the manifold is coupled to the flexible sheet using adhesives.

14. The wound drape of claim 12, wherein the manifold is coupled to the flexible sheet by bonding the manifold to the flexible sheet.

15. The wound drape of claim 12 further comprising a reduced-pressure interface.

16. The wound drape of claim 4, wherein the flexible sheet forms a frustoconical-shaped cavity.

17. A wound drape comprising:
    a flexible sheet formed of an impermeable elastomeric material and having an inner portion and an edge, the thickness of the flexible sheet gradually changes from the inner portion to the edge to provide the flexible sheet with anisotropic stretching properties such that the flexible sheet stretches more in a first direction than in a second direction;
    an adhesive coupled to the flexible sheet, wherein the adhesive is operable to couple the wound drape to a patient's epidermis; and
    a manifold coupled to the flexible sheet, the manifold configured to distribute a reduced pressure to a tissue site on the patient.

18. The wound drape of claim 17, wherein the manifold is coupled to the flexible sheet using adhesives.

19. The wound drape of claim 17, wherein the manifold is coupled to the flexible sheet by bonding the manifold to the flexible sheet.

20. The wound drape of claim 17, further comprising a reduced-pressure interface.

21. The wound drape of claim 17, wherein the flexible sheet forms a frustoconical-shaped cavity.

22. The wound drape of claim 17, wherein the inner portion is the substantial center of the wound drape.

23. The wound drape of claim 17, wherein the modulus of elasticity of the flexible sheet gradually changes from the inner portion to the edge.

24. The wound drape of claim 17, wherein the thickness of the flexible sheet gradually increases from the inner portion to the edge such that the edge is thicker than the inner portion.

25. The wound drape of claim 17, wherein the thickness of the flexible sheet gradually decreases from the inner portion to the edge such that the edge is thinner than the inner portion.

26. The wound drape of claim 17, wherein the adhesive is configured to transmit a closing force generated by the wound drape to the patient's epidermis.

27. The wound drape of claim 17, wherein the wound drape and the adhesive are configured to form a fluid seal over a tissue site on the patient.

28. The wound drape of claim 27, wherein the fluid seal is adapted to hold reduced pressure at the tissue site.

29. The wound drape of claim 17, wherein the flexible sheet is adapted to be coupled to a reduced-pressure source for treating a tissue site on the patient with reduced pressure.

30. The wound drape of claim 17, wherein the flexible sheet is comprised of transparent material.

\* \* \* \* \*